(12) United States Patent
Jacob et al.

(10) Patent No.: US 6,984,747 B2
(45) Date of Patent: Jan. 10, 2006

(54) METHOD FOR PREPARING STYRYL-FUNCTIONALIZED SILANES

(75) Inventors: Stéphane Jacob, Würzburg (DE); Lothar Fröhlich, Würzburg (DE); Konrad Olma, Höchberg (DE); Michael Popall, Würzburg (DE); Frank Kahlenberg, Brilon (DE)

(73) Assignee: Fraunhofer-Gesellschaft zur Forderung der Angewandten Forschung e.V., Munich (DE)

( * ) Notice: Subject to any disclaimer, the term of this patent is extended or adjusted under 35 U.S.C. 154(b) by 338 days.

(21) Appl. No.: 10/313,007

(22) Filed: Dec. 6, 2002

(65) Prior Publication Data

US 2003/0139621 A1 Jul. 24, 2003

(30) Foreign Application Priority Data

Dec. 16, 2001 (DE) ................................ 101 59 859

(51) Int. Cl.
*C07F 7/04* (2006.01)
(52) U.S. Cl. ...................................... 556/466; 556/480
(58) Field of Classification Search ............... 556/466, 556/480
See application file for complete search history.

(56) References Cited

U.S. PATENT DOCUMENTS 5,973,176 A 10/1999 Roscher et al.

FOREIGN PATENT DOCUMENTS

| GB | 1002129 A | 8/1965 |
| JP | 9328624 | 12/1997 |
| JP | 2002 179687 A | 6/2002 |

OTHER PUBLICATIONS

Kawakami et al., "Polymers with Oligoorganosiloxane Side Chains as Material for Oxygen Permeable Membranes," *Polymer J.* 17, pp. 1159 (1985).
Kawakami et al., "Poly. (*p*-disiloxane substituted styrene)s as materials for oxygen permeable membranes," *Polymer Comm.* 26, pp. 133-136 (1985).
Kawakami et al., "The Role of *p*-Oligosiloxane Substituents of Poilystyrene in Selective Oxygen Permeation through the Polymer Film," *Polymer Journal*, vol. 18 (3), pp. 237-241 (1986).
Kawakami et al., "Polystyrenes with Structurally Different Oligosiloxanes as *p*-Substituents for Oxygen Permeable Membrane Materials," *J. of Polymer Science: Part A: Polymer Chemistry*, vol. 25, pp. 3191-3204 1987.

*Primary Examiner*—Samuel Barts
(74) *Attorney, Agent, or Firm*—Hunton & Williams LLP

(57) ABSTRACT

The invention relates to a method for preparing silanes comprising styryl groups, said silanes being represented by the general formula (I):

$$(St)_b SiR'_a R_{4-a-b}$$

with improved yields through a reaction with magnesium in a solvent mixture comprising from 30:70 to 70:30 (v/v) of diethyl ether and tetrahydrofuran.

14 Claims, No Drawings

METHOD FOR PREPARING STYRYL-FUNCTIONALIZED SILANES

CROSS RELATED APPLICATION

This application claims the benefit of German application 10159859 filed Dec. 6, 2001 under 35 U.S.C. §119(a) and is hereby incorporated by reference in its entirety.

BACKGROUND

The present invention relates to a method for preparing styryl functionalized silanes, particularly alkoxy silanes. The methods according to the invention resulted in, markedly better yields than those obtained with usual methods.

Styryl-functionalized alkoxy silanes are used in a series of organically polymerizable silicic acid polycondensates which can for example be processed to colored particles (JP Patent 9328624), to oxygen permeable membranes (Y. Kawakami et al., Polymers with oligoorganosiloxane side chains as material for oxygen permeable membranes, Pol. J. 1985, 17, p. 1159 ff), or to electrophotographic materials (U.S. Pat. No. 4,716,091)

However, the preparation of styryl-functionalized silanes is not easy or simple. Kawakami, et al., proposed the preparation of a Grignard compound from styrene followed by a reaction with trichloromethylsilane. The silane compound reacts with the Grignard compound via the chlorine group. However, the product contains further chlorine groups which are highly reactive and either have to be hydrolyzed to hydroxy groups or be subjected to an alternative conversion. In Polym. Comm 26, 133 (1985), the same author describes the preparation of trimethylstyrylsilanes from a Grignard compound and trimethylchlorosilane. The reaction is reported to provide a yield of 36%. (See, Polym J. 17 (11), 1159–1172 (1985)).

The fluorinated styryl alkoxy silanes described in DE 196 13 650 A1 are likewise prepared using Grignard compounds. They can either contain a perfluorinated styryl group or only a perfluorinated phenylene ring. Example 1 provides a detailed description of the preparation of p-vinyl-tetrafluorophenyl-triethoxysilane: a Grignard compound is prepared in situ from perfluorinated bromostyrene and magnesium and reacted with an excess of tetraethoxysilane which is already present in the preparation. The reaction is effected at reflux temperature of diethyl ether. After separation of the magnesium salts and removal of the solvent, the residue is distillated. The synthetic pathway according to DE 196 13 650 A1 can, however, not be transferred to fluorine-free styryl derivates. This is because the formation of the corresponding Grignard reagent from bromostyrene occurs within a considerably shorter time and more exothermally than from the fluorinated derivative. Consequently, an explosive reaction course is to be expected since the Grignard compounds also react exothermally with alkoxy silanes. Moreover, the yield of the styryl-functionalized alkoxy silane obtained by this reaction is only 35%. Such a yield is unsatisfactory.

DETAILED DESCRIPTION OF THE PREFERRED EMBODIMENT

The present invention provides a simple and mild method for preparing styryl-functionalized silanes, by which method considerably improved yields are obtained.

This problem is solved by synthesizing the styryl-functionalized silanes via a Grignard reagent, similar to the prior art, but using chlorine-free alkoxy silanes as basic silane components and observing certain conditions. It has been found that the high reactivity of chlorosilanes has a negative effect on the selectivity of the substitution reaction and consequently, the yields described in prior art remained low. Further, it is decisive that the preparation of the Grignard compound on the one hand is effected at relatively mild conditions, and on the other hand should substantially be terminated before the reaction with the alkoxy silane takes place. The reaction temperatures of the latter should be controlled not to exceed about 20° C., preferably about 15° C. By selecting only one solvent for both steps, the requirements of having to isolate the Grignard reagent or of having to exchange the solvent can simultaneously be avoided in a preferable manner. Thus, the invention proposes to prepare the Grignard reagent in the presence of a solvent consisting of or substantially comprising a mixture of diethyl ether and tetrahydrofuran in a ratio of from 30:70 to 70:30, preferably of from 50:50 to 60:40. The reaction of the Grignard compound with the respective silane selected as educt should occur at controlled temperatures and not before the formation of the Grignard reagent has terminated. This reaction, the same or a similar solvent can suitably be used.

Therefore, it is an object of the invention to provide a method to for preparing silanes comprising styryl groups, said silanes being represented by the general formula (I):

$(St)_b SiR'_a R_{4-a-b}$ wherein the radicals and indices have the following meaning:

St represents a styryl group optionally substituted by a radical which contains carbon and which is bonded via one of its carbon atoms, for example alkyl, aryl, alkylaryl or arylalkyl, R is a group attached to the silicon atom via a carbon atom, for example substituted or unsubstituted alkyl, alkenyl, alkinyl, aryl, alkylaryl or arylalkyl, R' is an optionally substituted C alkoxy group, preferably methoxy, ethoxy, n- or iso-propoxy, n- or iso- or t-butoxy, a means 0, 1, 2 or 3 and b means 1, 2 or 3, characterized in that a compound represented by the formula StX, wherein X is a halogen that is attached to the phenyl ring of said styryl group and is preferably bromide or chlorine, is reacted with magnesium in a solvent mixture consisting of or substantially comprising diethyl ether and tetrahydrofuran in a ratio of from 30:70 to 70:30 (v/v) at a reaction temperature which does not exceed the boiling temperature of the mixture at ambient pressure, and in that subsequently, the Grignard reagent formed is reacted with a silane of the formula (II):

$$SiR'_{a+1} R_{3-a} \qquad (II)$$

wherein the radicals and indices have the same meaning as indicated for formula (I), at a maximum temperature of 20° C. in a solvent mixture substantially consisting of diethyl ether and tetrahydrofuran.

When preparing the Grignard reagent with the selected solvent mixture, a reaction temperature of preferably between about 40° C. and 55° C. can be achieved at ambient pressure, said temperature enabling the formation of said reagent within an appropriate period of time (if pure diethyl ether (boiling point 34.6° C.) is used as the mere solvent, a very low yield is obtained). On the other hand, the reaction temperature remains sufficiently low to avoid polymerization of the vinyl group (if pure tetrahydrofuran (boiling point: 65–67° C.) is used as the mere solvent, the yield decreases considerably). The reaction is exothermal; only after it has terminated and the solvent has cooled down, the silane component is added in accordance with the invention, said silane component preferably being dissolved in diethyl ether or in a mixture of diethyl ether and tetrahydrofuran. The latter is preferably effected at low temperatures, if required under cooling, in a range of from 0° C. to +10° C., the temperature possibly being higher, but not exceeding 20° C., more preferably not exceeding 15° C. in order to increase the selectivity of the reaction with a view to the desired products and to avoid dangerous development of heat. As soon as the substitution reaction has occurred to a considerable proportion, the temperature decreases again and the reaction stops. Therefore, the reaction mixture may subsequently be heated for some time, e.g. for some hours, e.g. at about 45° C., so that the substitution reaction is completed. As the maximum temperature in the second reaction step does not correlate with the boiling point of the solvent, the quantity ratio of the solvent used is of no importance, and usually it will be 30:70 to 90:10 (v/v) diethyl ether:tetrahydrofuran.

The proportion of the starting materials used will substantially determine the degree of substitution at the silane. An excess of the silane component relative to the desired degree of substitution is suitably applied. Thus, an excess of 100% of the silane component is preferably used, if a high yield of mono-styryl-substituted silane is desired, while an excess of 20% of the silane component is used, if a high yield of di-styryl-substituted silane is desired.

The method is particularly suited for the preparation of silanes comprising one or more and particularly one or two styryl groups which are preferably unsubstituted. Said styryl group(s) is/are preferably para-bonded to the silane. Besides said styryl group(s), the silane prepared according to the invention can additionally comprise one or more substituted or unsubstituted alkyl groups, one or more substituted or unsubstituted alkenyl groups, one or more substituted or unsubstituted alkinyl groups, or one or more substituted or unsubstituted aryl groups. Additionally or instead, alkoxy groups can be present, e.g. methoxy or ethoxy groups. The latter is preferred with a view to the possibility of incorporating styryl-functionalized alkoxy silanes into organically polymerizable silicic acid (hetero) condensates, as mentioned in the introductory part of the present specification.

As mentioned above, the process starts with the preparation of the Grignard reagent. For this purpose, a corresponding styrene halogenated at an appropriate position, preferably being brominated, or a corresponding compound containing styrene, is reacted with magnesium. Usually, magnesium shavings or cuttings can be used for this purpose; further, some iodine is added to the solution. Advantageously, the magnesium shavings are provided, situated in a suitable solvent, and the styrene compound dissolved in a solvent is added dropwise. Heating under reflux supports a rapid formation of the Grignard reagent.

After the reaction has terminated, the solution containing the Grignard reagent is contacted with a solution of the starting silane compound in an appropriate solvent, preferably in diethyl ether, and at lowest possible temperatures (e.g. 0–5° C.). Said silane compound can suitably be added dropwise. The above mentioned temperature ranges are to be observed. Ether can serve as solvent for the silane, as the temperatures of this reaction stage are below those of the preparation of the Grignard reagent.

After the conversion has terminated, the inorganic salts obtained are preferably removed, for example by precipitation with a very nonpolar solvent and filtration. The solvents are also removed, e.g. by stripping in a rotary evaporator. If required, the product is purified by distillation.

Fractionating distillation under vacuum and under the addition of a polymerization inhibitor as known in the art is a suitable distillation method. Appropriate polymerization inhibitors are 2,5-ditert-butyl hydroquinone, 2,6-di-tert-butyl-p-cresol or p-nitrosophenol, p-nitrosophenol being preferred. P-nitrosophenol does not pass over during distillation, so that pure products can be obtained.

In the following, the invention is described in more detail on the basis of examples.

EXAMPLE 1

Synthesis of p-vinyl phenyl methyl diethoxysilane

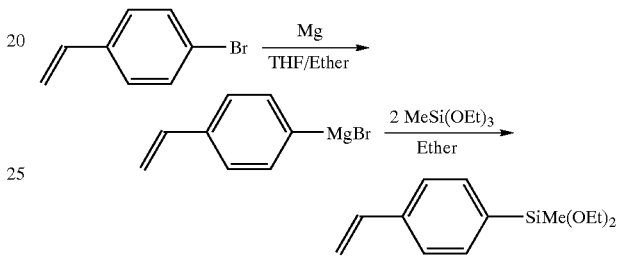

A mixture of 11.7 g (480 mmol) magnesium shavings and some iodine crystals in 40 ml of a solution A (55% diethyl ether, 45% tetrahydrofuran) is prepared in a three-neck flask by mechanical stirring under argon. Then, a solution of 80.0 g (436 mmol) bromostyrene, dissolved in 210 ml of said solvent mixture A, is slowly added dropwise in order to achieve a permanent exothermal reaction. The solvent is stirred under reflux at ambient pressure. After termination of said exothermal reaction, the reaction mixture is cooled down to 2° C., and subsequently, 155.5 g (872 mmol) methyl triethoxysilane in 160 ml dry diethyl ether is added; the temperature should not substantially exceed 15° C. After termination of the substitution reaction, stirring is continued over night at ambient temperature. Subsequently, about 200 ml n-heptane is added to obtain a precipitation of the magnesium salts. The magnesium salts are separated by filtration, 5.4 g (0.44 mmol) 4-nitrosophenol is added to the filtrate, the solvent is removed in a rotary evaporator, and the residue is subjected to a fractionating distillation under vacuum. 72.5 g (307 mmol) of the product was obtained.

Yield: 70.3%

Boiling point: 65–66° C. (0.05 mbar)

IR (film) 3089 (w), 3065 (w), 3009 (w), 2973 (m), 2925 (w), 2880 (m), 1630 (w), 1599 (m), 1545 (w), 1500 (w), 1482 (w), 1442 (w), 1391 (m), 1294 (w), 1258 (m), 1207 (w), 1166 (m), 1121 (s), 1106 (s), 1079 (s), 1029 (w), 1018 (w), 990 (m), 955 (m), 910 (m), 823 (m), 808 (s), 782 (m), 762 (s), 740 (w), 678 (m), 601 (w)

$^1$H-NMR (400.1 MHz, CDCl$_3$ δ=0.34 ppm (s, 3H, —Si—CH$_3$); 1.22 ppm (t, 6H, $^3$J=6.3 Hz, —O—CH$_2$—CH$_3$); 3.80 ppm (d, 4H, $^3$J=6.3 Hz, —O—CH$_2$—CH$_3$); 5.23 ppm (d, 1H, $^3$J(Z)=10.5 Hz, CH$_2$=CH—); 5.76 ppm (d, 1H, $^3$J(E)=17.1 Hz, CH$_2$=CH—); 6.68 ppm (dd, 1H, $^3$J=17.1, 10.5 Hz, CH$_2$=CH—); 7.39 ppm (d, 2H, $^3$Jo=6.5 Hz, H-2, H-5); 7.60 (d, 2H, $^3$Jo=7.0 Hz, H-2, H-6).

$^{13}$C-NMR (100.6 MHz, CDCl$_3$) δ=−4.1 ppm (1C, —Si—CH$_3$); 18.4 ppm (2C, —O—CH$_2$—CH$_3$); 58.5 ppm (2C, —O—CH$_2$—CH$_3$); 114.5 ppm (1C, CH$_2$=CH—); 125.7 ppm (2C, C-3, C-5 5);-); 134.3 ppm (2C, C-2, C-6); 134.5 ppm (1C, C-1); 136.9 ppm (1C, CH$_2$=CH—); 139.1 ppm (1C, C-4)

$^{29}$Si-NMR (79.5 MHz, CDCl$_3$) δ=−17.9 ppm

EXAMPLE 2

Synthesis of p-vinyl phenyl trimethoxysilane, bis-(p-vinyl phenyl)-dimethoxysilane and tris-(p-vinyl phenyl)-methoxysilane

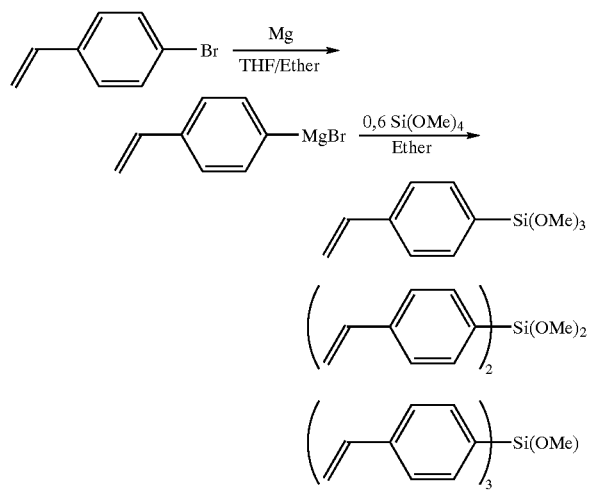

Styryl magnesium bromide is prepared in accordance with example 1. Subsequently, 39.9 g (262 mmol) tetramethoxysilane in 80 ml dried diethyl ether is added to the solvent of the Grignard reagent which has been cooled down to 2° C. Again, the temperature should not substantially exceed 15° C. When the addition is terminated and the temperature has again decreased to 5° C., the preparation is heated to 45° C. over one and a half hours in order to obtain a complete substitution. Stirring is continued over night at room temperature. The preparation is processed as described in example 1. After removal of the solvent, 105.3 g of a light yellow mixture is obtained. The $^{29}$Si-NMR-spectroscopy shows that the raw product contains p-vinyl phenyl trimethoxysilane, bis-(p-vinyl phenyl) dimethoxysilane and tris-(p-vinyl phenyl) methoxysilane.

The mono- and disubstituted alkoxy silanes are separated from the raw product by distillation and purified:

p-Vinyl phenyl trimethoxysilane (monosubstituted alkoxy silane) 15.8 g (70.5 mmol)
 Yield: 34.9%
 Boiling point: 59–60° C. (0.03 mbar)
 IR (film) 3067 (w), 2943 (m), 2841 (m), 1629 (w), 1600 (w), 1545 (w), 1463 (w), 1392 (w), 1192 (m), 1128 (s), 1089 (s), 991 (w), 914 (w), 808 (s), 714 (m), 606 (w)
 $^1$H-NMR (400.1 MHz, CDCl$_3$) δ=3.62 ppm (S, 9H, —O—CH$_3$); 5.29 ppm (d, 1H, $^3$J(Z) 10.0 Hz, CH$_2$=CH—); 5.81 ppm (d, 1H, $^3$J(E)=17.6 Hz, CH2=CH—); 6.72 ppm (dd, 1H, $^3$J=17.6, 10.0 Hz, CH$_2$=CH—); 7.43 ppm (d, 2H, $^3$J$_o$=6.5 Hz, H-2, H-5); 7.61 (d, 2H, $^3$J$_o$=7.0 Hz, H-2, H-6)

$^{13}$C-NMR (100.6 MHz, CDCl$_3$) δ=50.8 ppm (3C, —O—CH$_3$); 115.0 ppm (1C, CH$_2$=CH—); 125.8 ppm (2C, C-3, C-5);-); 128.8 ppm (1C, C-1); 135.1 ppm (2C, C-2, C-6); 136.7 ppm (1C, CH$_2$=CH—); 139.7 ppm (1C, C-4)

$^{29}$Si-NMR (79.5 MHz, CDCl$_3$) δ=−54.4 ppm

Bis-(p-vinyl phenyl)-dimethoxysilane (disubstituted alkoxy silane) 24.5 g (82.8 mmol)
 Yield: 41.0%
 Total yield 75.9
 IR (film) 3087 (w), 3065 (w), 3009 (m), 2965 (m), 2940 (m), 2838 (m), 1629 (w), 1599 (w), 1545 (w), 1500 (w), 1463 (w), 1420 (w), 1392 (m), 1295 (w), 1263 (w), 1191 (s), 1126 (s), 1083 (s), 1029 (w), 1018 (w), 990 (m), 913 (m), 834 (s), 807 (s), 754 (w), 733 (m), 715 (w), 652 (m), 634 (w), 598 (w)
 $^1$H-MNR (400.1 MHz, CDCl$_3$) δ=3.61 ppm (s, 6H, —O—CH$_3$); 5.26 ppm (d, 2H, $^3$J(Z) 10.0 Hz, CH$_2$=CH—); 5.79 ppm (d, 2H, $^3$J(E)=17.1 Hz, CH$_2$=CH—) 6.70 ppm (dd, 2H, $^3$J=17.1, 10.0 Hz, CH$_2$=CH—); 7.41 ppm (d, 4H, $^3$J$_o$=5.0 Hz, H$_{meta}$); 7.62 ppm (d, 4H, $^3$J$_o$=6.0 Hz, H$_{ortho}$)

$^{13}$C-NMR (100.6 MHz, CDCl$_3$) δ=50.9 ppm (2C, —O—CH$_3$) 114.8 ppm (2C, CH$_2$=CH—); 125.7 ppm (4C, C$_{meta}$); 131.8 ppm (2C, C—Si); 135.1 ppm (4C, C$_{para}$); 136.8 ppm (2C, CH$_2$=CH—); 139.4 ppm (2C, C$_{para}$)

$^{29}$Si-NMR (79.5 MHz, CDCl$_3$) δ=−29.0 ppm

Tris-(p-vinyl phenyl)-methoxysilane (raw product of the trisubstituted alkoxy silane)
 $^{29}$Si-NMR (79.5 MHz, CDCl$_3$) δ=−11.5 ppm

COMPARATIVE EXAMPLE 1

Synthesis of p-vinyl phenyl trimethoxysilane using diethyl ether as solvent

Styryl magnesium bromide is prepared in accordance with example 1, with the exception of using pure diethyl ether as the solvent. The substitution reaction is effected in accordance with example 2, with the exception of using 132.7 g (872 mmol) tetramethoxysilane. After distillation, 30.9 g (168.6 mmol) unreacted bromostyrene and 8.9 g (39.6 mmol) p-vinyl phenyl trimethoxysilane are obtained (Yield: 9.1%).

COMPARATIVE EXAMPLE 2

Synthesis of p-vinyl phenyl trimethoxysilane, using tetrahydrofurane as solvent for the preparation of the Grignard reagent.

Styryl magnesium bromide is prepared in accordance with example 1, with the exception of using tetrahydrofuran as the sole solvent. The substitution reaction is effected in accordance with comparative example 1. After distillation, 38.2 g (170.5 mmol) p-vinyl phenyl trimethoxysilan is obtained (Yield: 39.1%)

COMPARATIVE EXAMPLE 3

Synthesis of p-vinyl tetrafluorophenyl trimethoxysilane. The method of example 1 is repeated, however, using bromostyrene instead of bromotetrafluorostyrene. Methyl triethoxysilane is used instead of tetramethoxysilane. (Yield: 17%).

What is claimed is:

1. Method for preparing silanes comprising styryl groups, said silanes being represented by the general formula (I)

$$(St)_b SiR'_a R_{4-a-b}$$

wherein the radicals and indices have the following meaning:

St represents a styryl group which is unsubstituted or substituted by a radical containing at least one carbon atom which is bonded to the styryl group via one of its carbon atoms, R is a group attached to the silicon atom via a carbon atom, R' is an unsubstituted or substituted $C_{1-12}$-alkoxy group, a means 0, 1, 2 or 3 and b means 1, 2 or 3, comprising the following steps: (a) reacting a compound represented by the formula StX, wherein St is defined as above and X is a halogen that is attached to a phenyl ring of said styryl group with magnesium in a solvent mixture consisting of or substantially comprising diethyl ether and tetrahydrofuran in a ratio of from 30:70 to 70:30 (v/v) at a reaction temperature which does not exceed the boiling temperature of the mixture at ambient pressure to form a Grignard reagent, and (b) subsequently, reacting the Grignard reagent formed by step (a) with a silane of the formula (II)

$$SiR'_{a+1} R_{3-a} \quad (II)$$

wherein the radicals and indices have the same meaning as indicated for formula (I), at a maximum temperature of 20° C. in a solvent mixture substantially consisting of diethyl ether and tetrahydrofuran.

2. Method in accordance with claim 1, wherein said solvent substantially consists of diethyl ether and tetrahydrofuran in a ratio of from 50:50 to 60:40.

3. Method in accordance with claim 1, wherein the temperature at which said Grignard reagent formed is reacted with said silane of the general formula (II) does not exceed 15° C.

4. Method in accordance with claim 1, wherein salts are obtained which are at least partly separated and the solvent is removed, after the reaction has terminated, and wherein subsequently the product is subjected to a fractionating distillation.

5. Method in accordance with claim 4, wherein said fractionating distillation is effected in the presence of a polymerization inhibitor.

6. Method in accordance with claim 5, wherein the polymerization inhibitor is selected from the group consisting of 2,5-di-tert.-butylhydroquinone, 2,6-di-tert.-butyl-p-cresol and p-nitrosophenol.

7. Method in accordance with claim 6, wherein the polymerization inhibitor is p-nitrosophenol.

8. Method in accordance with claim 1, wherein said group (St) is a substituted or unsubstituted styryl group which is para-bonded to the silane.

9. Method in accordance with claim 8, wherein said group (St) is an unsubstituted styryl group.

10. Method in accordance with claim 1, wherein b is 1 or 2.

11. Method in accordance with claim 1, wherein the radical R of formula (I) is selected from the group consisting of substituted or unsubstituted $C_{1-12}$-alkyl, substituted or unsubstituted $C_{3-20}$-alkenyl, or -alkinyl and substituted or unsubstituted $C_{5-20}$-aryl, and wherein the radical R' of formula (I) means $C_{1-4}$-alkoxy.

12. Method in accordance with claim 11, wherein the radical R' is selected from the group consisting of methoxy and ethoxy.

13. Method in accordance with claim 11, wherein the radical R is selected from straight or branched or cyclic $C_{1-8}$-alkyl.

14. Method in accordance with claim 12, wherein the radical R is selected from the group consisting of methyl and ethyl.

* * * * *